US010781268B2

(12) United States Patent
Urech et al.

(10) Patent No.: US 10,781,268 B2
(45) Date of Patent: Sep. 22, 2020

(54) METHOD FOR DECREASING IMMUNOGENICITY

(71) Applicant: NOVARTIS AG, Basel (CH)

(72) Inventors: David Urech, Jona (CH); Leonardo Borras, Schlieren (CH)

(73) Assignee: Novartis AG, Basel (CH)

( * ) Notice: Subject to any disclaimer, the term of this patent is extended or adjusted under 35 U.S.C. 154(b) by 93 days.

(21) Appl. No.: 15/711,181

(22) Filed: Sep. 21, 2017

(65) Prior Publication Data

US 2018/0016350 A1 Jan. 18, 2018

Related U.S. Application Data

(62) Division of application No. 14/308,936, filed on Jun. 19, 2014, now Pat. No. 9,803,027, which is a division of application No. 12/973,968, filed on Dec. 21, 2010, now Pat. No. 8,796,425.

(60) Provisional application No. 61/289,446, filed on Dec. 23, 2009.

(51) Int. Cl.
*C07K 16/42* (2006.01)
*C07K 16/24* (2006.01)

(52) U.S. Cl.
CPC ............ *C07K 16/42* (2013.01); *C07K 16/241* (2013.01); *C07K 2317/24* (2013.01); *C07K 2317/34* (2013.01); *C07K 2317/622* (2013.01); *C07K 2317/76* (2013.01)

(58) Field of Classification Search
CPC .......... C07K 16/467; C07K 16/00–468; C07K 2317/622
See application file for complete search history.

(56) References Cited

U.S. PATENT DOCUMENTS

| | | | | |
|---|---|---|---|---|
| 6,815,540 | B1 | 11/2004 | Pluckthum et al. | |
| 8,293,235 | B2 | 10/2012 | Borras | |
| 8,673,310 | B2 | 3/2014 | Borras | |
| 8,796,425 | B2 * | 8/2014 | Urech .................. | C07K 16/241 530/387.3 |
| 8,937,162 | B2 | 1/2015 | Borras | |
| 9,422,366 | B2 | 8/2016 | Borras | |
| 9,556,265 | B2 | 1/2017 | Borras | |
| 9,803,027 | B2 * | 10/2017 | Urech .................. | C07K 16/241 |
| 2005/0069539 | A1 | 3/2005 | Cohen et al. | |
| 2006/0088539 | A1 | 4/2006 | Bander | |
| 2011/0268728 | A1 | 11/2011 | Borras | |
| 2014/0193400 | A1 | 7/2014 | Borras | |
| 2014/0221624 | A1 | 8/2014 | Borras | |
| 2016/0251428 | A1 | 9/2016 | Borras | |

FOREIGN PATENT DOCUMENTS

| | | | |
|---|---|---|---|
| WO | 199318792 | | 9/1993 |
| WO | 2005016967 | A2 | 2/2005 |
| WO | 2009000098 | | 12/2008 |
| WO | 2009103969 | A1 | 8/2009 |
| WO | 2009155725 | | 12/2009 |
| WO | 2009155726 | A2 | 12/2009 |

OTHER PUBLICATIONS

ABK81278, GenBank, Jul. 14, 2016; first submitted Aug. 26, 2006.
Souza et al., J. Immunol. 2007; 179:3153-60.
Holliger & Hudson, Nature Biotech, 2005; 23(9): 1126-36.
Hwang & Foote, Methods, 2005; 36:3-10.
Presta, Adv. Drug Deilv. Rev., 2006; 28:640-56.
Jung, Sabine, et al; "Selection of improved protein statibtlity by phage display", J. Mol. Biol., 1999, vol. 294, p. 163-180.
Borras, Leonardo, Prosecution History, Utility U.S. Appl. No. 13/000,460, filed Dec. 21, 2010, 3,095 pages.
Pavlinkova et al.; Effects of Humanization and Gene Shuffling on Immunogenicity and Antigen Binding of Anti-Tag-72 Single-Chain FVs; Int. J. Cancer; (2001); 94; pp. 717-726; Wiley-Lisss, Inc.
Xiong et al.; "Engineering vaccines with heterologus B and T cell epitopes using immunoglobulin genes"; Nature; Biotechnology, vol. 15; No. 9; pp. 882-886 (Sep. 1, 1997).
Search report and written opinion corresponding to PCT application No. PCT/CH2010/000326, dated Mar. 31, 2011.
Dumoulin et al.; "Single-domain antibody fragments with high conformational stability"; Protein Science; vol. 11, pp. 500-515 (2002).
Hamers-Casterman et al; "Naturally occurring antibodies devoid of light chains"; Letters to Nature; Nature; vol. 363; pp. 446-448 (Jun. 3, 1993).
Honegger and Pluckthun; "Yet another numbering scheme for immunoglobulin variable domains: an automatic modeling and analysis tool"; J. Mol. Biol.; vol. 309; pp. 657-670 (2001).
Knappik et al.; "Fully synthetic human combinatorial antibody libraries (HuCAL) based on modular consensus frameworks and CDRs randomized with trinucleotides"; J. Mol. Biol.; vol. 296; pp. 57-86 (2000).
Kushner et al.; "High-dose cyclophosphamide inhibition of humoral immune response to murine monoclonal antibody 3F8 neuroblastoma patients: broad implications for immunotherapy"; Pediatr Blood Cancer; vol. 48, pp. 430-434 (2007).
Leonard et al; "Abbreviated chemotherapy with fludarabine followed by tositumomab and iodine I 131 tositumomab for untreated folicular lymphoma"; Journal of Clinical Oncology; vol. 23; No. 24; pp. 5696-5704 (Aug. 20, 2005).
Molineux; "Pegylation: Engineering Improved Biopharmaceuticals for Oncology"; Pharmacotherapy; vol. 23; vol. 8 part 2; pp. 3S-8S (2003).
Nagata and Pastan; "Removal of B cell epitopes as a practical approach for reducing immunogenicity of foreign protein-based therapeutics"; Advanced Drug Delivery Reviews; vol. 61; pp. 977-985 (2009).

(Continued)

*Primary Examiner* — Jessica H Roark
(74) *Attorney, Agent, or Firm* — Jason J. Derry; Novartis AG

(57) ABSTRACT

A method for decreasing the immunogenicity of antibody variable domains is disclosed.

5 Claims, 5 Drawing Sheets
Specification includes a Sequence Listing.

(56) References Cited

OTHER PUBLICATIONS

Nieba et al.; "Disrupting the hydrophobic patches at the antibody variable/constant domain interface: improved in vivo folding and physical characterization of an engineered scFv fragment"; Protein Engineering; vol. 10; No. 4; pp. 435-444 1997).
Onda et al; "An immunotoxin with greatly reduced immunogenicity by identification and removal of B cell epitopes"; PNAS; vol. 105; No. 2; pp. 11311-11316 (Aug. 12, 2008).
Ward et al.; "Binding activities of a repertoire of single immunoglobulin variable domains secreted from *Escherichia coli"*; Letters to Nature; Nature; vol. 341; pp. 544-546 (Oct. 12, 1989).
Stephan Duebel "Handbook of Therapeutic Antibodies", Chapter 6, Molecular Engineering I: Humanization, Wiley-VCH, Weinheim, 119-144, 2007.

* cited by examiner

VL SEQUENCES

Solvent exposed residues different from scFv903

| Residue position (AHo) | 1 | 10 | 15 | 20 | 24 | 27 | 30 | 32 | 33 | 40 | 48 | 58 | 68 | 69 | 70 | 72 | 81 | 83 | 88 | 90 | 99 | 101 | 111 | 133 | 134 | 146 | 148 | 149 |
|---|---|---|---|---|---|---|---|---|---|---|---|---|---|---|---|---|---|---|---|---|---|---|---|---|---|---|---|---|
| 903 | E | T | V | I | Q | E | I | H | S | W | P | L | S | T | L | S | S | S | E | T | D | F | L | S | T | T | L | G |
| 791 | E | T | L | I | Q | Q | S | Y | G | W | S | Q | S | K | L | S | S | S | E | S | D | F | N | T | G | T | L | G |
| 961 | E | T | V | I | Q | E | I | H | S | W | P | L | S | T | L | S | S | S | E | T | D | F | L | S | T | T | L | G |
| 105 | D | S | V | T | T | Q | S | S | N | D | P | S | F | N | R | T | R | Y | D | T | E | V | . | . | N | E | K | R |
| 903 | | | | | | | | | | | | | | | | | | | | | | | | | | | | |
| 791 (g) | | | X | | | X | X | X | X | | X | X | | X | | | | | | X | | | X | X | X | | | |
| 961 (a) | | | | | | | | | | | | | | | | | | | | | | | | | | | | |
| 105 (b) | X | X | | X | X | X | X | X | X | X | | X | X | X | X | X | X | X | X | | X | X | | | X | X | X | X |
| Categorie | β | β | γ | β | β | βγ | βγ | βγ | βγ | β | γ | βγ | β | βγ | β | β | β | β | β | γ | β | β | γ | γ | βγ | β | β | β |
| Percentage of human sera that showed binding to the respective epitope categorie | 48% | 48% | 88% | 48% | 48% | NA | NA | NA | NA | 48% | 88% | NA | 48% | NA | 48% | 48% | 48% | 48% | 48% | 88% | 48% | 48% | 88% | 88% | NA | 48% | 48% | 48% |

Figure 3

VH SEQUENCES
Solvent exposed residues different from scFv903

| Residue position (AHo) | 1 | 10 | 11 | 12 | 14 | 20 | 30 | 33 | 38 | 40 | 65 | 66 | 67 | 69 | 72 | 73 | 76 | 79 | 83 | 86 | 92 | 94 | 97 | 98 | 99 | 103 | 110 | 111 | 112 | 134 | 144 |
|---|---|---|---|---|---|---|---|---|---|---|---|---|---|---|---|---|---|---|---|---|---|---|---|---|---|---|---|---|---|---|---|
| 903 | E | G | G | L | Q | R | S | D | Y | Y | D | D | D | Y | T | W | G | T | D | K | Q | N | R | A | E | V | D | H | N | W | L |
| 791 | E | G | G | L | Q | R | T | R | S | W | D | I | T | L | N | W | G | P | D | K | Q | N | R | A | E | V | G | Y | A | Y | L |
| 961 | E | G | G | S | Q | R | S | D | Y | Y | D | D | D | Y | T | W | G | T | D | K | Q | N | R | A | E | T | D | H | N | W | T |
| 105 | Q | A | E | V | K | K | T | H | . | G | T | G | E | T | D | K | D | T | E | A | E | T | T | S | D | V | R | G | . | D | L |
| 903 | | | | | | | | | | | | | | | | | | | | | | | | | | | | | | | |
| 791 (g) | | | | | | | X | X | X | X | | X | X | X | X | | | X | | | | | | | | | X | X | X | X | |
| 961 (a) | | | | X | | | | | | | | | | | | | | | | | | | | | | X | | | | | X |
| 105 (b) | X | X | X | X | X | X | X | X | X | X | X | X | X | X | X | X | X | | X | X | X | X | X | X | X | | X | X | X | X | |
| Categorie | β | β | β | αβ | β | β | βγ | βγ | βγ | βγ | γ | βγ | βγ | βγ | βγ | β | β | γ | β | β | β | β | β | β | β | α | βγ | βγ | βγ | βγ | α |
| Percentage of human sera that showed binding to the respective epitope categorie | 48% | 48% | 48% | 23% | 48% | 48% | NA | NA | NA | NA | 88% | NA | NA | NA | NA | 48% | 48% | 88% | 48% | 48% | 48% | 48% | 48% | 48% | 48% | 35% | NA | NA | NA | NA | 35% |

Figure 4

SEQUENCE LISTING

<160> NUMBER OF SEQ ID NOS: 4

<210> SEQ ID NO 1
<211> LENGTH: 251
<212> TYPE: PRT
<213> ORGANISM: Artificial
<220> FEATURE:
<223> OTHER INFORMATION: antibody fragment

<400> SEQUENCE: 1

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Asp Pro Tyr Tyr Ala
            180                 185                 190

Thr Trp Ala Lys Gly Arg Phe Thr Ile Ser Arg Asp Thr Ser Lys Asn
        195                 200                 205

Thr Val Tyr Leu Gln Met Asn Ser Leu Arg Ala Glu Asp Thr Ala Val
    210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250
```

<210> SEQ ID NO 2
<211> LENGTH: 254
<212> TYPE: PRT
<213> ORGANISM: Artificial
<220> FEATURE:
<223> OTHER INFORMATION: antibody fragment

<400> SEQUENCE: 2

```
Met Glu Ile Val Met Thr Gln Ser Pro Ser Thr Leu Ser Ala Ser Leu
1               5                   10                  15

Gly Asp Arg Val Ile Ile Thr Cys Gln Ser Ser Gln Ser Val Tyr Gly
            20                  25                  30

Asn Ile Trp Met Ala Trp Tyr Gln Gln Lys Ser Gly Lys Ala Pro Lys
        35                  40                  45
```

-continued

Leu Leu Ile Tyr Gln Ala Ser Lys Leu Ala Ser Gly Val Pro Ser Arg
50 55 60

Phe Ser Gly Ser Gly Ser Gly Ala Glu Phe Ser Leu Thr Ile Ser Ser
65 70 75 80

Leu Gln Pro Asp Asp Phe Ala Thr Tyr Tyr Cys Gln Gly Asn Phe Asn
85 90 95

Thr Gly Asp Arg Tyr Ala Phe Gly Gln Gly Thr Lys Leu Thr Val Leu
100 105 110

Gly Gly Gly Gly Gly Ser Gly Gly Gly Gly Ser Gly Gly Gly Gly Ser
115 120 125

Gly Gly Gly Gly Ser Glu Val Gln Leu Val Glu Ser Gly Gly Gly Leu
130 135 140

Val Gln Pro Gly Gly Ser Leu Arg Leu Ser Cys Thr Ala Ser Gly Phe
145 150 155 160

Thr Ile Ser Arg Ser Tyr Trp Ile Cys Trp Val Arg Gln Ala Pro Gly
165 170 175

Lys Gly Leu Glu Trp Val Ala Cys Ile Tyr Gly Asp Asn Asp Ile Thr
180 185 190

Pro Leu Tyr Ala Asn Trp Ala Lys Gly Arg Phe Pro Val Ser Thr Asp
195 200 205

Thr Ser Lys Asn Thr Val Tyr Leu Gln Met Asn Ser Leu Arg Ala Glu
210 215 220

Asp Thr Ala Val Tyr Tyr Cys Ala Arg Leu Gly Tyr Ala Asp Tyr Ala
225 230 235 240

Tyr Asp Leu Trp Gly Gln Gly Thr Leu Val Thr Val Ser Ser
245 250

<210> SEQ ID NO 3
<211> LENGTH: 245
<212> TYPE: PRT
<213> ORGANISM: Artificial
<220> FEATURE:
<223> OTHER INFORMATION: antibody fragment

<400> SEQUENCE: 3

Asp Ile Val Met Thr Gln Ser Pro Ser Ser Leu Ser Ala Ser Val Gly
1 5 10 15

Asp Arg Val Thr Leu Thr Cys Thr Ala Ser Gln Ser Val Ser Asn Asp
20 25 30

Val Val Trp Tyr Gln Gln Arg Pro Gly Lys Ala Pro Lys Leu Leu Ile
35 40 45

Tyr Ser Ala Phe Asn Arg Tyr Thr Gly Val Pro Ser Arg Phe Ser Gly
50 55 60

Arg Gly Tyr Gly Thr Asp Phe Thr Leu Thr Ile Ser Ser Leu Gln Pro
65 70 75 80

Glu Asp Val Ala Val Tyr Tyr Cys Gln Gln Asp Tyr Asn Ser Pro Arg
85 90 95

Thr Phe Gly Gln Gly Thr Lys Leu Glu Val Lys Arg Gly Gly Gly Gly
100 105 110

Ser Gly Gly Gly Gly Ser Gly Gly Gly Gly Ser Ser Gly Gly Gly Ser
115 120 125

Gln Val Gln Leu Val Gln Ser Gly Ala Glu Val Lys Lys Pro Gly Ala
130 135 140

Ser Val Lys Val Ser Cys Thr Ala Ser Gly Tyr Thr Phe Thr His Tyr
145 150 155 160

-continued

```
Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 4
<211> LENGTH: 251
<212> TYPE: PRT
<213> ORGANISM: Artificial
<220> FEATURE:
<223> OTHER INFORMATION: antibody fragment

<400> SEQUENCE: 4

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Val Glu Ser Gly Gly Gly Ser Val Gln
    130                 135                 140

Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Asp Pro Tyr Tyr Ala
            180                 185                 190

Thr Trp Ala Lys Gly Arg Phe Thr Ile Ser Arg Asp Thr Ser Lys Asn
        195                 200                 205

Thr Val Tyr Leu Gln Met Asn Ser Leu Arg Ala Glu Asp Thr Ala Thr
    210                 215                 220

Tyr Tyr Cys Ala Gly Gly Asp His Asn Ser Gly Trp Gly Leu Asp Ile
225                 230                 235                 240

Trp Gly Gln Gly Thr Thr Val Thr Val Ser Ser
                245                 250
```

METHOD FOR DECREASING IMMUNOGENICITY

CROSS-REFERENCE TO RELATED APPLICATION

This application is a divisional of U.S. patent application Ser. No. 14/308,936, filed Jun. 19, 2014 (now U.S. Pat. No. 9,803,027), which is a divisional of U.S. patent application Ser. No. 12/973,968, filed Dec. 21, 2010 (now U.S. Pat. No. 8,796,425), which claims priority to U.S. Provisional Patent Application Ser. No. 61/289,446 filed Dec. 23, 2009, the entire contents of which are incorporated herein by reference.

FIELD OF THE INVENTION

This invention relates to a method of altering the immunogenicity of antibody variable domains, in particular of scFvs.

BACKGROUND ART

Therapeutic antibodies administered to a subject in need are often recognized as foreign by the subject's immune system. Even if the administered antibodies have been humanized, e.g. by grafting of murine CDRs into human immunoglobulin frameworks to minimize the mouse component, they still may elicit an immune response which compromises the efficacy and/or safety of the therapeutic.

According to the literature antibody responses in patients are dependent on the presence of both B-cell epitopes and T-cell epitopes. When a B-cell receptor recognizes and binds an antigen such as an administered therapeutic antibody, the antigen is internalized into the B cell by receptor-mediated endocytosis and undergoes proteolytic processing. The resulting peptides are subsequently presented by MHC class II molecules. Upon recognition of the T cell epitope by a T helper cell, the latter stimulates the corresponding B cells to proliferate and differentiate into antibody producing plasma cells.

In order to decrease the response of the patient's immune system to the administered antibodies, the prior art has provided several de-immunization techniques. Most of the current approaches focus on the removal of T-cell epitopes, whereas there are only limited examples of methods to reduce B-cell immunogenicity.

WO 93/18792 describes a process for the modification of antibodies by partial reduction of the antibody. This alters their immunogenicity so that their ability to induce an anti-isotypic response is selectively diminished, while they remain able to elicit an anti-idiotypic response. Albeit the method would be suitable for vaccines, anti-idiotypic responses are not desirable for other therapeutic applications.

Molineux G (2003) Pharmacotherapy 23: 35-85 describes the coupling of proteins to high-molecular-weight polyethylene glycol. However, Onda, M. et al (2008), PNAS Vol 105(32): 11311-11316 have reported a limited success of this approach with hybrid proteins composed of the variable fragment attached to a bacterial or plant toxin. Their hybrid proteins were inactivated; moreover, they found only a minor decrease in immunogenicity.

A second approach consists in chemotherapy prior to antibody administration, wherein patients are treated with cyclophosphamide or fludarabine. This approach is not desirable for the patients as the treatment damages the immune system (Kusher, B H et al (2007), Pediatr Blood Cancer 48: 430-434; Leonard J P et al (2005), J Clin Oncol 23: 5696-5704).

Nataga, S. and Pastan, I. (2009), Adv Drug Deliv Rev, p. 977-985 and Onda, M. et al (2008), PNAS Vol 105(32): 11311-11316 propose point mutations at "antigenic hot spots" on the foreign protein surface, thereby removing the B-cell epitope. They substituted bulky hydrophilic residues with large exposed areas by small amino acids (alanine, glycine and serine). Alanine is preferred for substitution as it is typically present in buried and exposed positions of all secondary structures and also does not impose new hydrogen bonding. Alanine lacks side chain atoms after the β-carbon that can react with antibodies and moreover maintains the conformation of the antigen. However, said "hot spots" described by Nataga and Pastan are conformational epitopes which are located in discrete clusters on the protein surface. Extensive experimental work is needed to determine the locations of the epitopes that could not be reproduced in a computer simulation and thus, their method does not represent a general solution to reduce immunogenicity of antibodies that can be applied routinely. Furthermore, a principle assumption of this method is that mainly hydrophilic residues on the molecular surface are involved in the contact with the host antibody. For most foreign proteins this is in fact true, however in cases were only portions (e.g. fragments, domains) of a naturally occurring protein is used, it may well be that also hydrophobic amino acids, formerly shielded by the contact to other domains become exposed to the solvent and present as epitope to the immune system. This is explicitly the case for Fv antibody fragments, where the interface residues on the variable domain are covered in the Fab fragment but are exposed in isolated variable domains. Currently available algorithms to predict B cell epitopes are poorly validated and typically have a low rate of success.

Thus, there is a need in the art to provide straight forward methods which effectively reduce the immunogenicity of antibody fragments and particularly for the variable domains.

SUMMARY OF THE INVENTION

Hence, it is a general object of the invention to provide a method to decrease the immunogenicity of any antibody variable domain without the need to perform extensive molecular modeling efforts. In particular, it is an object of the invention to provide a method to remove B-cell epitopes from antibody variable domains.

Accordingly, the invention provides method for decreasing the immunogenicity of antibody variable domains comprising a variable light chain and/or a variable heavy chain, wherein the method comprises the step of substituting one or more amino acid residues of the variable light chain and/or the variable heavy chain, said residue being present at the interface between the variable chain and the constant chain of a corresponding full-length antibody or Fab.

In one aspect, the antibody variable domain is an scFv, an Fv fragment or a single domain antibody, in particular an scFv.

In one aspect, one or more amino acid residues of the variable light chain and/or the variable heavy chain to be substituted are consensus residues of the respective subtype.

In another aspect, the one or more amino acid residues to be substituted are Leucine (L), Valine (V), Aspartic acid (D), Phenylalanine (F), Arginine (R) and/or Glutamic Acid (E).

In certain aspects, the one or more amino acid residues of the variable light chain are at positions 99, 101 and/or 148 (AHo numbering). In other aspects, the one or more amino acid residues of the variable heavy chain are at one or more positions 12, 97, 98, 99, 103, and/or 144 (AHo numbering).

In still another aspect, the one or more amino acid residues to be substituted in the variable heavy chain is (a) Leucine (L) at heavy chain amino acid position 12; (b) Valine (V) at heavy chain amino acid position 103; and/or (c) Leucine (L) at heavy chain amino acid position 144.

In another aspect, the invention provides antibody variable domains obtainable by the method disclosed herein, and pharmaceutical compositions comprising said antibody variable domains.

BRIEF DESCRIPTION OF THE DRAWINGS

The invention will be better understood and objects other than those set forth above will become apparent when consideration is given to the following detailed description thereof. Such description makes reference to the annexed drawings.

FIG. 3 shows a variable light chain sequence alignment of solvent exposed positions of four different scFvs. Upper panel: amino acids in each scFv differing in type from the respective amino acid in scFv 903 are given in bold. The lower panel indicates the epitope category to which each individual position was associated, and the percentage of human sera that showed binding to the respective epitope category.

FIG. 4 shows a variable heavy chain sequence alignment of solvent exposed positions of four different scFvs. Upper panel: amino acids in each scFv differing in type from the respective amino acid in scFv 903 are given in bold. The lower panel indicates the epitope category to which each individual position was associated, and the percentage of human sera that showed binding to the respective epitope category.

DISCLOSURE OF THE INVENTION

Figures 1A, 1B:
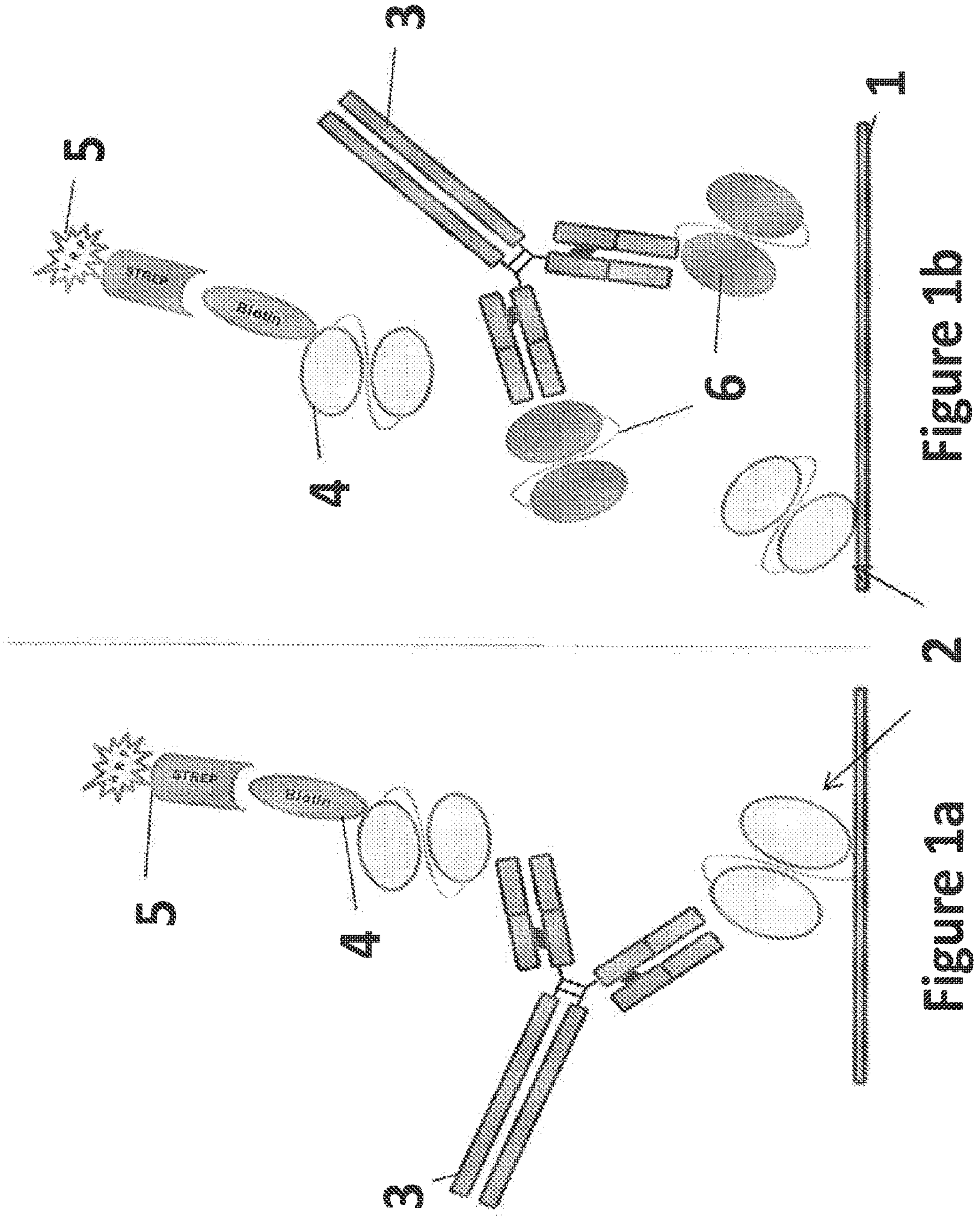
FIG. 1*a* shows a schematic view of the bridging ELISA used to detect pre-existing anti-scFv antibodies. 1: plate surface, 2: scFv903; 3: Anti-Drug Antibody (ADA); 4: biotinylated scFv903; 5: Streptavidin Poly-HRP (Horse Radish Peroxidase).
FIG. 1*b* shows the principle for confirmation assessment where ADA binding to the drug and biotinylated scFv903 was competed with an excess of scFv903, 34 max (791), scFv903 DHP (961) and scFv105 (100 mcg/ml).

So that the invention may be more readily understood, certain terms are first defined. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

The expression "immunogenicity" as used herein means the occurrence of B cell or antibody epitopes on a protein administered to a subject, whereas such B cells or antibodies (also referred to as anti-drug antibodies; ADAs) may have existed prior to the administration of said protein.

The extent of such immunogenicity can be determined by an ELISA assay and can be expressed as the percentage of human sera that contain measurable amounts of pre-existing ADAs. A reduction of immunogenicity between a protein and a corresponding protein being engineered with the goal to reduce its immunogenicity can be measured by comparing the percentage of serum samples containing ADAs against the engineered protein with the percentage of serum samples containing ADAs against the original protein. A lower number or percentage of positive serum samples for the engineered protein indicates a reduction of immunogenicity for the engineered protein. A more sensitive measurement, which can be applied on the basis of a single serum sample, employees a competition ELISA setup. In such competition ELISA the engineered protein competes with the original protein for binding of ADAs in the test serum. The lower the ability of the engineered protein to compete with the original protein, the more successful the immunogenicity was reduced.

Preferably, the extent of immunogenicity reduction is referred to as percentage of serum samples in which the engineered protein is no more able to effectively compete with the original protein. Effective competition is defined by a threshold (a relative signal from the competition ELISA), whereas −100 indicates a perfect competitor (no reduction of immunogenicity) and 0 indicates no competition at all (complete absence of ADA epitopes). Typically, such threshold for effective competition can be −90, −80, −70, −60, 50, −40, −30, −20, −10 or >−10.

"Interface" or "interface-interface" as used herein refers to those regions localized between the variable domains and the constant regions 1 (CL1 or CH1) of a full length antibody or between the Fab portion and the Fc domain (CH2 and CH3).

"ADA", as used herein, is an abbreviation for anti-drug antibodies which refers to pre-existing antibodies in the serum or sera of patients.

The term "antibody variable domain" (V-Domain) refers to a molecule that contains all or a part of the antigen binding site of an antibody, e.g., all or part of the heavy and/or light chain variable domain, such that the antibody variable domain specifically recognizes a target antigen. The term thus corresponds to the V-J-REGION or V-D-J-REGION of the immunoglobulin. These V-Domains are designated as: VL (V-Domain of an Ig-light chain) or VH (V-Domain of an Ig-heavy chain). Non-limiting examples of antibody variable domains include (i) Fv fragments comprising the $V_L$ and $V_H$ domains of a single arm of an antibody, (ii) single chain Fv fragments (scFvs), (iii) single domain antibodies such as Dab fragments (Ward et al., (1989) Nature 341:544-546), which consist of a VH or a VL domain, Camelid (see Hamers-Casterman, et al., Nature 363:446-448 (1993), and Dumoulin, et al., Protein Science 11:500-515 (2002)) or Shark antibodies (e.g., shark Ig-NARs Nano-Bodies®).

The term "antibody framework" or "framework" as used herein refers to the part of the variable domain, either VL or VH, which serves as a scaffold for the antigen binding loops of this variable domain (Kabat, E. A. et al., (1991) Sequences of proteins of immunological interest. NIH Publication 91-3242).

The term "antibody CDR" or "CDR" as used herein refers to the complementarity determining regions of the antibody which consist of the antigen binding loops as defined by Kabat E. A. et al., (1991) Sequences of proteins of immunological interest. NIH Publication 91-3242). Each of the two variable domains of an antibody Fv fragment contain, for example, three CDRs.

The term "single chain antibody" or "scFv" refers to a molecule comprising an antibody heavy chain variable region ($V_H$) and an antibody light chain variable region ($V_L$) connected by a linker. Such scFv molecules can have the general structures: $NH_2$-$V_L$-linker-$V_H$-COOH or $NH_2$-$V_H$-linker-$V_L$-COOH.

The term "subtype" refers to a set of V-DOMAINS which belong to the same group, in a given species, and which share high percentage of identity. The term "subtype" refers to the subtype defined by the respective consensus sequence as defined in Knappik (2000). The term "subfamily" or "subclass" is used as synonym for "subtype". The term "subtype" as used herein refers to sequences sharing the highest degree of identity and similarity with the respective consensus sequence representing their subtype. To which "subtype" a certain variable domain belongs to is determined by alignment of the respective sequence with either all known human germline segments or the defined consensus sequences of the respective subtype and subsequent association to a certain subtype based on greatest homology. Methods for determining homologies and grouping of sequences by using search matrices, such as BLOSUM (Henikoff 1992) are well known to the person skilled in the art.

The "consensus residue" at a given position can be determined by generating the amino acid consensus sequence of a given subtype. "Amino acid consensus sequence" as used herein refers to an amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids. The amino acid sequence of a protein can be analyzed at various levels. For example, conservation or variability can be exhibited at the single residue level, multiple residue level, multiple residue with gaps etc. Residues can exhibit conservation of the identical residue or can be conserved at the class level. Other classes are known to one of skill in the art and may be defined using structural determinations or other data to assess substitutability. In that sense, a substitutable amino acid can refer to any amino acid which can be substituted and maintain functional conservation at that position. As used herein, when one amino acid sequence (e.g., a first VH or VL sequence) is aligned with one or more additional amino acid sequences (e.g., one or more VH or VL sequences in a database), an amino acid position in one sequence (e.g., the first VH or VL sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

The AHo numbering scheme used throughout the description is described in A. Honegger and A. Plückthun (2001), J. Mol. Biol. 309: 657-670.

The term "patient" refers to a human or to a non-human animal.

The term "treat", "treating" or "treatment" refers to therapeutic and/or preventive measures with the aim to prevent, cure, delay, reduce the severity of or ameliorate one or more symptoms of the disorder or recurring disorder, or in order to prolong the survival of a subject beyond that expected in the absence of such treatment.

"Hydrophilic" amino acids are polar and electrically charged amino acids, such as Asp, Glu, Lys, Arg and His.

Amino acids that are polar and uncharged are Gly, Ser, Thr, Cys, Asp, Gln and Tyr.

"Hydrophobic" amino acids are typically non polar amino acids such as Ala, Val, Leu, Ile, Met, Phe, Trp and Pro.

In a first aspect, a method for decreasing the immunogenicity of an antibody variable domain is disclosed. The antibody variable domain comprises a variable light chain and/or a variable heavy chain, and the method comprises the step of substituting one or more amino acid residues of the variable light chain and/or the variable heavy chain, said residue being present at the interface between the variable chain and the constant chain of a corresponding full-length antibody (or Fab, i.e. any antibody or antibody fragment comprising a constant domain or parts thereof).

Said one or more amino acid residues selected for substitution are preferably those which are present at the interface between the variable chain and the constant chain of the corresponding full-length antibody (or Fab, i.e. any antibody or antibody fragment comprising a constant domain or parts thereof) and are solvent exposed in an antibody variable domain, such as a scFv. Said interface is also termed V/C domain interface.

The antibody variable domain is e.g. an scFv, an Fv fragment or a single domain antibody, preferably a scFv.

Of particular interest are the amino acid residues at positions that form discontinuous, i.e. conformational, B-cell epitopes. Such residues include those found at the following positions (AHo numbering):

variable light chain positions 99, 101 and/or 148; and variable heavy chain positions 12, 97, 98, 99, 103, and/or 144.

Residue positions 99, 101 and 148 (AHo numbering) of the light chain, as well as residue positions 12, 98, 103, and 144 (AHo numbering) of the heavy chain: are known from Nieba et al. (1997) Protein Eng., April; 10(4):435-44 (also disclosed in U.S. Pat. No. 6,815,540) for improving folding behavior of antibodies by protein engineering. Nieba proposes to substitute hydrophobic amino acids by hydrophilic ones at the indicated positions; however, the document is silent that these substitutions may have an influence on the immunogenicity of the molecule. Moreover, the authors highlight that not all of these hydrophobic residues are equally good candidates for replacements. While the existence of the hydrophobic patches is preserved in all antibodies, their exact position and extent varies.

As known in the art, in particular amino acids which (i) are present in a turn region of the secondary structure, (ii) have a large, flexible side chain or a bulky side chain, or (iii) are hydrophobic are prone to be part of a B-cell epitope and thus elicit an immunogenic reaction. By removing immunogenic amino acids, B-cell epitopes are interrupted and the patient's tolerance to the antibody variable domain can be enhanced.

Preferably, the selected one or more amino acid residues are substituted by an amino acid which is less immunogenic than the selected amino acids, i.e. does not elicit an immune response or elicits a weak immune response. Such less immunogenic amino acids are those that reduce ADA reactivity compared with ADA reactivity to the antibody variable domain containing the original (i.e. un-substituted) amino acid.

Immunogenicity, i.e. the property to induce an antibody response within the patient's body, can e.g. be predicted by its antigenicity, i.e. the reactivity with pre-existing antibodies. The antigenicity may e.g. be determined by ADA reactivity via a bridging ELISA (see example 1 and FIG. 1), using sera from donors which potentially comprise pre-existing antibodies. Hence, for the evaluation of less immunogenic amino acids, the antibody variable domain may be mutated at the indicated positions. The effect of such mutations on immunogenicity can be assessed by competing the signal of the progenitor antibody in the bridging ELISA with the presumably less immunogenic, engineered derivative thereof, as described herein. Binding of ADAs against an antibody can also be assessed by the use of label-free binding assays, such as surface Plasmon resonance, fluorescence resonance energy transfer (FRET), calorimetric assays and others.

In one embodiment, amino acids chosen for being substituted are at one or more positions selected from the group consisting of variable light chain residues 99, 101 and 148 and variable heavy chain residues 12, 97, 98, 99, 103 and 144.

Preferred amino acids chosen for substitutions are surface exposed but would be hidden by the constant domain in a corresponding full-length antibody or Fab.

In one embodiment, the one or more amino acid residues of the variable light chain and/or the variable heavy chain to be substituted are consensus residues of the respective subtype. For example, preferred amino acids chosen for substitutions are Leucine (L), Valine (V), Aspartic acid (D), Phenylalanine (F), Arginine (R), and/or Glutamic Acid (E).

More preferably, the one or more amino acid residues chosen for being substituted are selected from the group consisting of variable light chain residues D99, F101 and L148 and variable heavy chain residues L12, R97, A98, E99, V103 and L144.

Even more preferably, Leucine (L), Valine (V), Phenylalanine (F) and/or Alanine (A) are substituted by polar amino acids, preferably by serine (S) and/or threonine (T).

In particular, the DHP motif as described in PCT/CH2009/00022 has been unexpectedly found to decrease the immunogenicity of antibody variable domains without having an adverse effect on the thermal stability, the refolding, the expression yield, the aggregation and/or the binding activity of the antibody variable domain. Said DHP motif comprises the amino acid residues of the variable heavy chain 12, 103 and 144 (AHo numbering) at which the following amino acids are present:

(a) Serine (S) at heavy chain amino acid position 12;

(b) Serine (S) or Threonine (T) at heavy chain amino acid position 103; and/or (c) Serine (S) or Threonine (T) at heavy chain amino acid position 144.

PCT/CH2009/00022 does not provide any hint that the taught modifications are suitable to decrease the immunogenicity of antibody variable domains.

The DHP motif is located at the V/C interface of a Fab fragment and becomes solvent exposed upon removal of the constant domains. Thus in a preferred embodiment of the present invention, one or more amino acid residues are selected for substitution from the group consisting of the variable heavy chain 12, 103 and 144 (AHo numbering). Preferably, (a) Leucine (L) is present at heavy chain amino acid position 12;

(b) Valine (V) is present at heavy chain amino acid position 103; and/or (c) Leucine (L) is present at heavy chain amino acid position 144.

These residues are highly conserved in human frameworks. Thus, substituting one or more of said residues provides a general solution to de-immunize antibody variable domains without affecting the biophysical properties of the molecule, and the method disclosed herein is applicable to any framework of an antibody variable domain. Preferably, the residues present at the indicated position(s) are substituted by (a) Serine (S) at heavy chain amino acid position 12;

(b) Serine (S) or Threonine (T) at heavy chain amino acid position 103; and/or (c) Serine (S) or Threonine (T) at heavy chain amino acid position 144.

Even more preferably, the following substitutions are made: L12S, V103T and/or L144T.

The antibody variable domain may be directed against any target, and specifically binds said target. Exemplary examples of targets include, but are not limited to: a transmembrane molecule, a receptor, a ligand, a growth factor, a growth hormone, a clotting factor, an anti-clotting factor, a plasminogen activator, a serum albumin, a receptor for a hormone or a growth factor, a neurotrophic factor, a nerve growth factor, a fibroblast growth factor, transforming growth factor (TGF), a CD protein, an interferon, a colony stimulating factor (CSF), an interleukin (IL), a T-cell receptor, a surface membrane protein, a viral protein, a tumor associated antigen, an integrin or an interleukin, VEGF; a renin; a human growth hormone; a bovine growth hormone; a growth hormone releasing factor; parathyroid hormone; thyroid stimulating hormone; a lipoprotein; alpha-1-antitrypsin; insulin A-chain; insulin B-chain; proinsulin; follicle stimulating hormone; calcitonin; luteinizing hormone; glucagon; clotting factor VIIIC; clotting factor IX; tissue factor (TP); von Willebrands factor; Protein C; atrial natriuretic factor; a lung surfactant; urokinase; human urine; tissue-type plasminogen activator (t-PA); bombesin; thrombin; hemopoietic growth factor; tumor necrosis factor-alpha or -beta; enkephalinase; RANTES (Regulated on Activation Normally T-cell Expressed and Secreted); human macrophage inflammatory protein (MIP-1)-alpha; human serum albumin; Muellerian-inhibiting substance; relaxin A-chain; relaxin B-chain; prorelaxin; mouse gonadotropin-associated peptide; a microbial protein, beta-lactamase; DNase; IgE; a cytotoxic T-lymphocyte associated antigen (CTLA); CTLA-4; inhibin; activin; vascular endothelial growth factor (VEGF); protein A or D; a rheumatoid factor; bone-derived neurotrophic factor (BDNF); neurotrophin-3, -4, 5, or -6

(NT-3, NT-4, NT-5, or NT-6); NGF-beta; platelet-derived growth factor (PDGF); aFGF; bFGF; epidermal growth factor (EGF); TGF-alpha; TGF-beta, including TGFbeta1, TGF-beta2, TGF-beta3, TGF-beta14, or TGF-beta5; insulin-like growth factor-I or -II (IGF-I or IGF-II); des(1-3)-IGF-I (brain IGF-I), an insulin-like growth factor binding protein, erythropoietin; an osteoinductive factor; an immunotoxin; a bone morphogenetic protein (BMP); interferon-alpha, -beta, or -gamma; M-CSF, GM-CSF or G-CSF; IL-1 to IL-10; superoxide dismutase; decay accelerating factor; an AIDS envelope protein; a transport protein; a homing receptor; an addressin; a regulatory protein; CD3, CD4, CD8, CD11a, CD11b, CD11c, CD18, CD19, CD20, CD34, CD40, or CD46, an ICAM, VLA-4 or VCAM; or HER2, HER3 or HER4 receptor; a member of the ErbB receptor family; an EGF receptor; HER2, HER3 or HER4 receptor; a cell adhesion molecule; LFA-1, Mac1, p150.95, VLA-4, ICAM-1, VCAM, alpha4/beta7 integrin or alphav/beta3 integrin; an alpha or beta subunit of a cell adhesion molecule; antibodies); a growth factor, VEGF; tissue factor (TF); TGF-beta; alpha interferon (alpha-IFN); IL-8; IgE; blood group antigens Apo2, death receptor; flk2/flt3 receptor; obesity (OB) receptor; mpl receptor; CTLA4 or protein C.

In another embodiment, the invention provides an antigen binding fragment obtainable by the method disclosed herein. Said antigen binding fragment may e.g. be used for therapeutic or diagnostic applications.

The sequences used in the Examples herein include:

```
>903 or 578minmax
                                        (SEQ ID NO: 1)
EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN

FGQGTKLTVLGGGGGSGGGGSGGGGSGGGGSEVQLVESGGGLVQPGGSLR

LSCTASGFSLTDYYYMTWVRQAPGKGLEWVGFIDPDDDPYYATWAKGRFT

ISRDTSKNTVYLQMNSLRAEDTAVYYCAGGDHNSGWGLDIWGQGTLVTVS

S

>791 or 34max
                                        (SEQ ID NO: 2)
MEIVMTQSPSTLSASLGDRVIITCQSSQSVYGNIWMAWYQQKSGKAPKLL

IYQASKLASGVPSRFSGSGSGAEFSLTISSLQPDDFATYYCQGNFNTGDR

YAFGQGTKLTVLGGGGGSGGGGSGGGGSGGGGSEVQLVESGGGLVQPGGS

LRLSCTASGFTISRSYWICWVRQAPGKGLEWVACIYGDNDITPLYANWAK

GRFPVSTDTSKNTVYLQMNSLRAEDTAVYYCARLGYADYAYDLWGQGTLV

TVSS

>scFv105
                                        (SEQ ID NO: 3)
DIVMTQSPSSLSASVGDRVTLTCTASQSVSNDVVWYQQRPGKAPKLLIYS

AFNRYTGVPSRFSGRGYGTDFTLTISSLQPEDVAVYYCQQDYNSPRTFGQ

GTKLEVKRGGGGSGGGGSGGGGSSGGGSQVQLVQSGAEVKKPGASVKVSC

TASGYTFTHYGMNWVRQAPGKGLEWMGWINTYTGEPTYADKFKDRFTFSL

ETSASTVYMELTSLTSDDTAVYYCARERGDAMDYWGQGTLVTVSS

>961 or 578minmaxDHP
                                        (SEQ ID NO: 4)
EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN
```

-continued

```
FGQGTKLTVLGGGGGSGGGGSGGGGSGGGGSEVQLVESGGGSVQPGGSLR

LSCTASGFSLTDYYYMTWVRQAPGKGLEWVGFIDPDDDPYYATWAKGRFT

ISRDTSKNTVYLQMNSLRAEDTATYYCAGGDHNSGWGLDIWGQGTTVTVS

S
```

Example 1

Anti-Drug-Antibody bridging ELISA (ADA-ELISA)

1.1 Background

Pre-existing antibodies against a monoclonal antibody may be either directed to constant regions, to variable domain framework positions or to the antigen binding loops, the CDRs. Pre-existing antibodies binding specifically to Fv fragments but not to IgGs are likely to recognize regions that were formerly shielded in the IgG. Such regions are mainly the domain interfaces localized between the variable domains and the constant regions 1 (CL1 or CH1) or between the Fab portion and the Fc domain (CH2 and CH3). Antibodies that recognize such interfaces are format specific in all likelihood. Since the framework sequence of scFv903 is highly conserved in humans, it appears likely that the pre-existing antibodies to scFv903 in human sera either bind to CDRs or to V/C-interface residues. The epitopes for such pre-existing anti-scFv903 antibodies were characterized in a sandwich ELISA by assessing the potential of a variety of scFvs to compete with binding of anti-drug antibodies (ADA) to ESBA903. The scFvs tested were:

- scFvs containing the same framework as scFv903 but different CDRs (34_max (791)),
- scFvs with a different framework than scFv903 and different CDRs (scFv105), and
- an scFv903 variant (scFv903 DHP (961)) containing substitutions in the former V/C interface.

The ELISA developed for screening of anti-scFv903 antibodies is a quasi-quantitative assay and was developed in a bridging format (see FIG. 1) which allows detection of responses of all antibody isotypes from different species.

Briefly and with reference to FIG. 1, microtitre plates were coated with scFv 903 1, 2 to which samples containing anti-scFv 903 antibodies 3,6 were bound. As a first detection agent, biotinylated scFv 903 4 was used to detect any bound scFv 903/anti-scFv 903 complexes which in turn were detected by a second detection agent 4, Streptavidin Poly-HRP 5. The amount of anti-scFv 903 antibodies present in the quality control and samples was determined using peroxidase (POD) substrate (3,3'-5,5'Tetramethylbenzidine (TMB)).

The development of the ADA ELISA was performed with a positive control antibody termed AB903-3. The Anti-scFv 903 antibody stock (rabbit polyclonal Anti-scFv 903 IgG termed AB903-3) was developed by immunization of rabbit with scFv 903 and subsequent affinity-purification of the serum (Squarix Biotechnology). As depicted in FIG. 1*b*, epitopes of pre-existing antibodies on scFv 903 were characterized by competition of ADA binding to scFv 903 with the scFvs describe above.

1.2 Assay Procedure

A microtitre plate (Nunc Maxisorp) was coated with 0.1 mcl/ml scFv 903 in PBS (Dulbecco, Sigma). The sealed plate was incubated overnight at 4° C.

The plate was washed three times with 300 mcl/well wash buffer (TBST 0.005% Tween (20) in an Atlantis Microplate Washer (ASYS). Non-specific sites were blocked with 280 mcl/well blocking buffer (PBS, 10 mg/ml BSA 1% (w/v), 0.1 ml/50 ml Tween 20 (0.2%, v/v). The sealed plate was incubated for 1.5 hours at room temperature (25° C.) with shaking. Subsequently, the plate was again washed three times as indicated above.

The analyte control (either an affinity purified rabbit polyclonal Anti-scFv 903 IgG termed AB903-3 or human sera) was added in three different concentrations:

HiQC: 2500 ng/ml AB903

MeQC: 500 ng/ml AB903

LoQC: 250 ng/ml AB903

QC were spiked in the respective NSB serum pool (pool of all sera used for determination of the assay cut point, >30). The samples to be measured were applied in a 1 to 10 dilution. 50 mcl of sample were applied per well; the sealed plate was incubated 2.0 hours at room temperature (25° C.).

As indicated above, the plate was washed three times with washing buffer. As a first detection agent, biotinylated scFv 903 (500 mcg protein biotinylated with Lightning-Link kit (protocol: Lightning-Link™ Biotin Conjugation Kit, Type A, #704-0015, Innova Biosciences) was added. For said purpose, biotinylated scFv 903 was diluted in dilution buffer at a concentration of 250 ng/ml (PBS, 10 mg/mL BSA 1% (w/v), 0.1 ml/50 ml Tween 20 (0.2% v/v)). 50 mcl/well was added. The sealed plate was incubated 1.0 hour at room temperature (25° C. nominal) under shaking.

The plate was again washed three times as indicated above. The second detection agent, Streptavidin-Poly-HRP (Stereospecific Detection Technologies, 1 mg/ml) was diluted 1:5'000 in dilution buffer and 50 mcl were added per well. The sealed plate was incubated 1.0 hour at room temperature (25° C. nominal) under shaking.

For the detection, the plate was washed three times with 300 mcl/well wash buffer as indicated above. Subsequently, the plate was washed twice with 300 mcL/well ddH2O. Then, 50 mcl/well POD (TMB) substrate at room temperature was added. After incubation for 3-6 minutes (the maximal incubation time of 30 min should not be exceeded), the reaction was stopped by adding 50 mcl/well 1M HCL. If the color reaction was very intense, the reaction was stopped earlier by 50 mcl/well 1M HCL.

Using a microtiter plate reader from Tecan Sunrise, the plate was read at 450 nm. Typically, the reaction was performed in triplicate for each quality control, NSB and individual serum sample. The readings were averaged.

1.3 Assay Cut Point (ACP) Determination

For determination of positives, an assay cut point was established during assay development. The cut point of an assay is the level of response of the assay at or above which a sample is defined to be positive and below which it is defined to be negative. Using a risk-based approach, it is appropriate to have 5% false positives, rather than any false negatives. This was done with a parametric approach using the mean absorbance plus 1.645 Standard deviations, where 1.645 is the 95th percentile of the normal distribution. All individuals with OD≥3* standard deviation were excluded and a new assay cut point was calculated. If ODs of maximally 5% of the individuals are above the ACP, the calculated value can be used as ACP. In the contrary, the exclusion criteria to the remaining individuals were applied again and the process was repeated until maximally 5% of the individuals had an OD above the ACP.

Figure 2:
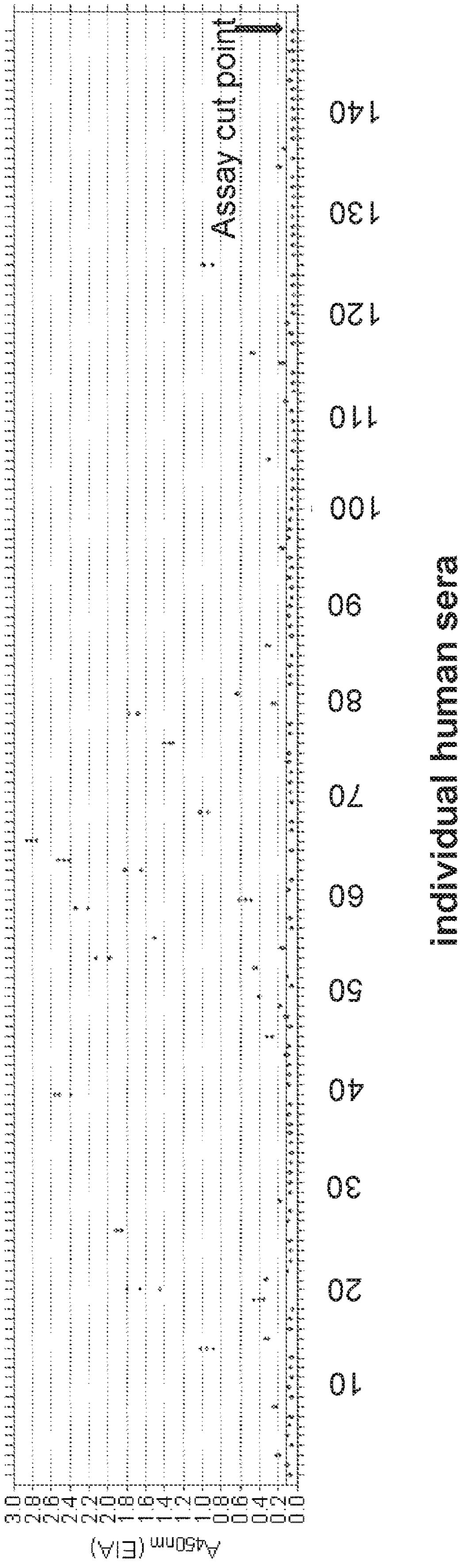
FIG. 2 shows signal intensity of 149 individual sera in a colorimetric assay (briding ELISA) to detect anti-scFv 903 antibodies. Signals above the assay cut point indicate presence of anti-scFv 903 antibodies (ADAs) in the respective serum sample. Roughly 30% of tested sera samples were positive in the assay.

After exclusion of 34 out of 149 individual sera, the assay cut point was corrected to 0.110. 40 sera (26.8%) showed an OD higher than the assay cut point (see FIG. 2). LoQC, MeQC and HiQC samples were included for monitoring of assay performance. For preparation of the NSB the 34 sera removed for statistical evaluation of the assay cut point were excluded from the serum pool. The mean NSB result was 0.073 resulting in a normalisation factor of 1.50.

1.4 Determination of Normalisation Factor and Plate Specific Cut Point

Once an ACP was determined with a NSB, the normalisation factor was applied to calculate the plate specific cut point for subsequent measurements with the same NSB. To determine the normalisation factor, the OD values of a NSB were assessed. Three replicates (triplicates) of the NSB were analysed on each plate. The normalisation factor was defined as the assay cut point divided by the mean absorbance of NSB. The plate specific cut point for each plate was calculated as follows:

Plate specific cut point=NSB absorbance*normalisation factor.

1.5 Confirmatory Assay

In case of detected ADAs in the serum, a confirmatory assay proves that the antibodies found to be positive in the ADA bridging ELISA are specific to scFv 903. The confirmatory assay was similar to the screening assay, except that positive samples were mixed and pre-incubated with assay buffer containing scFv 903 or just assay buffer prior to analysis. For this purpose, reference material was spiked in dilution buffer or human serum to a concentration of the LoQC, MeQC and HiQC level. These samples were then diluted 1 in 2 with either buffer or buffer containing 10 mcg/ml, 100 mcg/ml or 1 mcg/ml (for human serum) scFv 903. Samples were incubated at RT for approximately 60 minutes to allow binding of scFv 903 to ADAs present in the sample. Samples were diluted further in buffer prior to loading onto the plate in order that the overall matrix dilution was at the minimum. scFv 903 prevents binding of the ADAs to scFv 903 coated on the plate (see also FIG. 1). Therefore, a change in OD values of >30% between sera diluted 1 in 2 with buffer and sera diluted 1 in 2 with buffer containing scFv 903 was defined as minimal inhibition to confirm presence of specific anti-scFv 903 antibodies. Pre-incubation with scFv 903 at 10 mcg/ml, 100 mcg/ml as well as 1 mcg/ml resulted in OD changes between 60% and 95% for all 3 QC levels tested. A concentration of 100 mcg/ml was selected for the confirmation assay.

1.6 Results of the Competition Assay

In order to map the binding sites of anti-scFv 903 antibodies, a set of different scFvs with known amino-acid sequences as well as the IgG format of scFv903 was used instead of excess scFv 903 in the confirmatory assay set up described above. In this experimental setup, a given test antibody can only compete for binding of scFv 903 to anti-scFv 903 antibodies (ADAs), if the ADAs recognize a similar epitope also on the test scFv. Thus, a signal reduction in the assay would indicate the presence of at least one epitope that is shared between scFv 903 and test scFv. The following test antibodies have been used in this experiment: scFv105, a humanized TNF-inhibitory scFv antibody fragment containing mouse CDRs grafted onto a human scFv scaffold of the type Vk1-VH1b; scFv 791, a humanized TNF-inhibitory antibody fragment containing rabbit CDRs grafted on the same scFv scaffold as used for scFv 903 (Vk1-VH3); scFv 961, a derivative of scFv 903 containing three point mutations (the DHP-motif) in the region participating in the interface between variable and constant domain, and scFv903-IgG, the IgG format of scFv 903.

Correlation of sequence variations between the four tested molecules with differences in ADA binding characteristics was used to identify ADA epitopes in the entire scFv scaffold and more specifically in the V-C interface. In addition, competition with a full-size version of scFv903 (IgG) was used to further confirm the format specificity of the pre-existing ADAs.

A summary of data from competition experiments is shown in table 1. Binding of all but two individual human sera was competed with an excess of scFv903 confirming that these ADAs were specific for ESBA903. Out of the 32 human sera specific for scFv 903 only two were not competed by scFv791, indicating that the antibodies present in these human sera (H53 and H76) bind to scFv903 CDRs, while all other sera apparently were not CDR specific. About 48% of ADAs did also recognize epitopes on scFv105, although these responses were slightly lower. This suggested that most of the antibodies are not explicitly framework specific but rather bind to amino acids conserved in different scFv scaffolds. Interestingly, the IgG format of scFv 903 did not significantly compete with scFv 903 for binding to any of the sera tested. This strongly suggests that the majority of sera bind to the interface between variable and constant region, which is accessible to ADAs in scFv 903 but not in the IgG format thereof. Furthermore, scFv 961, differing in only three amino acids from scFV903 competed binding of only 64% of the ADAs. These responses were generally lower than with scFV903, which implies that the predominant fraction of pre-existing ADAs bind to to an epitope comprising these three amino acids that constitute a hydrophobic surface patch in the V-C interface of scFv 903. The difference between results obtained with scFV105 compared to scFV903 can be explained by the presence of different patterns of hydrophobic surface patches in these two molecules. In summary, these results show that up to 50% of pre-existing ADAs in human sera represent scFv format specific antibodies.

TABLE 1

Epitope characterization of pre-existing antibodies in human sera. % reduction in OD upon competition with 100 mcg/ml of scFv903, 791 (34_max), scFv105 and 961 (scFv903_DHP) and the IgG format of scFv903 are given for 34 different human sera with pre-existing anti-scFv903 antibodies.

| human sera | % reduction 903 | % reduction791 | % reduction105 | % reduction961 |
|---|---|---|---|---|
| H3 | −79.9 | −85.0 | −58.8 | −1.7 |
| H8 | −87.3 | −90.7 | −23.1 | −88.6 |
| H14 | −96.6 | −96.5 | −3.6 | na |
| H15 | −91.1 | −90.0 | −69.5 | na |
| H19 | −90.3 | −84.3 | −73.5 | −63.7 |
| H20 | −91.9 | −96.1 | −18.8 | −23.5 |
| H21 | −85.4 | −85.3 | −3.4 | −80.5 |
| H26 | −92.0 | −96.8 | −79.9 | 0.1 |
| H29 | −79.4 | −78.7 | −51.4 | −21.9 |
| H40 | −95.4 | −94.6 | 3.5 | −1.7 |
| H46 | −79.8 | −77.1 | −66.7 | −40.1 |
| H49 | −82.7 | −81.2 | −26.1 | −8.8 |
| H50 | −88.7 | −88.5 | −31.1 | −72.8 |
| H53 | −32.4 | −34.6 | −18.4 | −30.9 |
| H54 | −93.1 | −91.7 | −61.3 | −69.4 |
| H55 | −89.4 | −96.0 | −71.9 | −14.7 |
| H56 | −24.4 | −15.1 | −4.8 | −23.8 |
| H59 | −97.0 | −96.4 | −93.7 | −67.3 |
| H60 | −95.6 | −94.8 | −10.8 | −1.2 |
| H63 | −96.8 | −19.7 | −80.5 | −35.9 |
| H64 | −96.9 | −95.5 | −55.5 | −13.7 |
| H66 | −97.2 | −96.4 | −2.6 | na |
| H69 | −92.2 | −74.7 | −87.6 | −6.2 |
| H76 | −97.0 | −48.6 | −65.7 | −36.4 |
| H79 | −97.1 | −96.8 | −40.5 | −74.1 |
| H80 | −87.0 | −85.3 | −50.9 | −55.1 |
| H81 | −94.7 | −94.4 | −18.1 | −8.8 |

TABLE 1-continued

Epitope characterization of pre-existing antibodies in human sera. % reduction in OD upon competition with 100 mcg/ml of scFv903, 791 (34_max), scFv105 and 961 (scFv903_DHP) and the IgG format of scFv903 are given for 34 different human sera with pre-existing anti-scFv903 antibodies.

| human sera | % reduction 903 | % reduction791 | % reduction105 | % reduction961 |
|---|---|---|---|---|
| H86 | −86.2 | −86.7 | Na | −67.9 |
| H96 | −80.3 | −78.5 | −29.0 | −78.0 |
| H105 | −97.2 | −96.9 | 2.4 | 7.4 |
| H115 | −94.7 | −94.8 | −60.4 | −31.4 |
| H116 | −97.8 | −97.2 | −43.4 | −33.2 |
| H125 | −97.9 | −97.4 | −55.5 | 2.7 |
| H135 | −92.5 | −95.2 | −23.1 | −74.7 |

To identify the interaction sites between ADAs and scFv 903, sequence variations between scFv 903 and the other scFvs (791, 105 and 961) were correlated with the specificities of ADAs in the various human sera. In a first step the sequences of the different scFvs were aligned and solvent exposed positions were grouped according to sequence differences between scFv 903 and the other scFvs (FIGS. 3 and 4). Herein, "α" represents the group of positions which differ between scFv 961 and all other scFvs, "β" stands for positions at which only scFv105 differs in sequence from the other molecules, and "γ" indicates positions at which scFv 791 is different from all others. Further αβ and αγ describe positions that are conserved in all scFvs except scFv 961 and scFv105 or scFv961 and scFv791, respectively. Similarly, human sera containing anti-scFv903 antibodies were classified by their specificity to the other scFvs as determined in the competition assay, using the same classification code as used above for the amino acid positions (see table 2). In order for a serum to qualify as binding to a given test scFv a minimal signal reduction of 50% in the competition assay was set as treshold. In this study "α" represents human anti-scFv 903 sera that did not show binding activity towards scFv 961. "β"-sera did not bind to scFv105 and "γ"-sera did not bind to scFv 791. From the correlation of sequence analysis and in vitro binding studies it can be concluded that for example anti-scFv 903 antibodies in a type "α" human serum interact with at least one amino acid from the amino acid group "α". Similarly, sera of any other type interact with at least one amino acid in the respective amino acid group.

The structural analysis and homology model of scFv 903 were done using Discover Studio version 2.5.5. The modeled structure was analyzed to determine which amino acid residues are exposed to solvent, and which amino acid residues are buried. The calculation was done by determining the relative Solvent Accessible Surface (SAS) of each residue with respect to their maximum possible solvent accessible surface area. The cutoff was defined as 25%, therefore residues with a relative SAS equal or more than 25% were considered solvent exposed.

TABLE 2

Results of an ELISA in which scFv 903, 791, scFv105 and 961 compete with scFv903 for binding to the antibodies in 34 serum samples.

| Human serum | scFv903 | scFv791 | scFv105 | scFv961 | Antigenic region |
|---|---|---|---|---|---|
| H125 | −98 | −97 | −55 | 3 | α |
| H116 | −98 | −97 | −43 | −33 | αβ |

TABLE 2-continued

Results of an ELISA in which scFv 903, 791, scFv105 and 961 compete with scFv903 for binding to the antibodies in 34 serum samples.

| Human serum | scFv903 | scFv791 | scFv105 | scFv961 | Antigenic region |
|---|---|---|---|---|---|
| H105 | −97 | −97 | 2 | 7 | αβ |
| H79 | −97 | −97 | −41 | −74 | β |
| H26 | −92 | −97 | −80 | 0 | α |
| H14 | −97 | −96 | −4 | nd | nd |
| H66 | −97 | −96 | −3 | nd | nd |
| H59 | −97 | −96 | −94 | −67 | All |
| H20 | −92 | −96 | −19 | −23 | αβ |
| H55 | −89 | −96 | −72 | −15 | α |
| H64 | −97 | −96 | −55 | −14 | α |
| H135 | −93 | −95 | −23 | −75 | β |
| H60 | −96 | −95 | −11 | −1 | αβ |
| H115 | −95 | −95 | −60 | −31 | α |
| H40 | −95 | −95 | 4 | −2 | αβ |
| H81 | −95 | −94 | −18 | −9 | αβ |
| H54 | −93 | −92 | −61 | −69 | All |
| H8 | −87 | −91 | −23 | −89 | β |
| H15 | −91 | −90 | −69 | nd | nd |
| H50 | −89 | −89 | −31 | −73 | β |
| H86 | −86 | −87 | nd | −68 | nd |
| H80 | −87 | −85 | −51 | −55 | All |
| H21 | −85 | −85 | −3 | −81 | β |
| H3 | −80 | −85 | −59 | −2 | α |
| H19 | −90 | −84 | −73 | −64 | All |
| H49 | −83 | −81 | −26 | −9 | αβ |
| H29 | −79 | −79 | −51 | −22 | α |
| H96 | −80 | −79 | −29 | −78 | β |
| H46 | −80 | −77 | −67 | −40 | α |
| H69 | −92 | −75 | −88 | −6 | α |
| H76 | −97 | −96 | −18 | −36 | αγ |
| H53 | −32 | −35 | −18 | −31 | none |
| H63 | −97 | −20 | −80 | −36 | αγ |
| H56 | −24 | −15 | −5 | −24 | none |

94% of the sera had antibodies that bound specifically to scFv 903 or to scFv 791, showing that most pre-existing antibodies did not bind to CDRs regions. Half (50%) of the human sera did not show or had less antibodies that bind to scFv 961. Sequence analysis revealed that scFv 961 and scFv 903 differ only at positions 12, 103 and 144 in the variable heavy chain. Thus L12, V103 and L144 in the variable heavy chain of scFv 903 are involved in ADA binding (table 2 and FIGS. 4 and 5). This finding was further confirmed by the fact that the IgG format of scFv 903, in which the respective interface residues are not solvent accessible due to the contact with the adjacent constant region, did not compete with binding of anti-scFv 903 sera to scFv 903.

12% of tested human sera had antibodies against all antigenic regions (α,β,γ).

64% of the sera did not contain or had significantly less antibodies that bind to scFv 961 (α). As described above, this scFv differs from scFv 903 only in 3 residue positions (L12S, V103T, L103T) located at the former variable-constant domain interface. Since these residue positions at the V/C interface are highly conserved, mutating these positions already presents a general solution to de-immunize scFvs without affecting the biophysical properties.

Figures 5A, 5B:
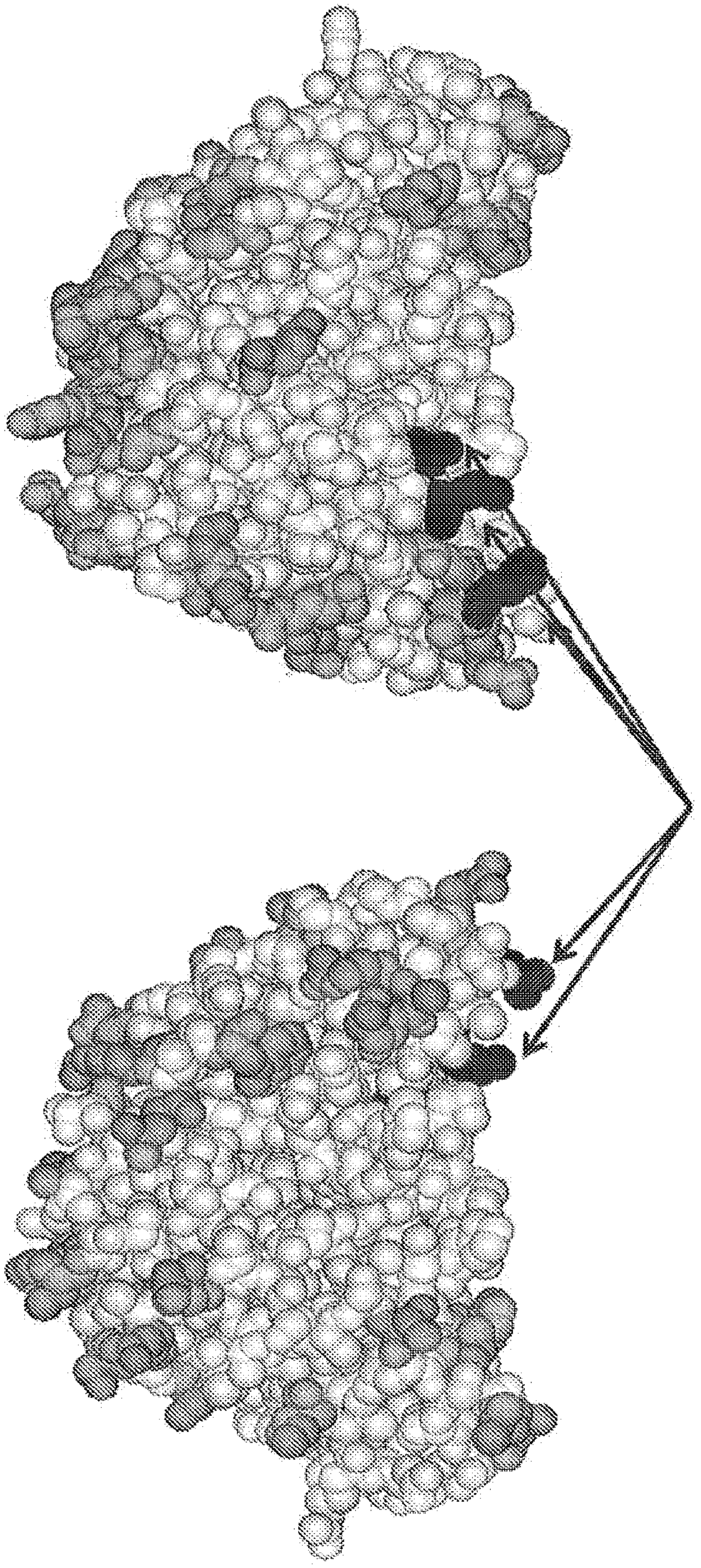
FIG. 5 shows the modeled molecular structure of scFv 903. 5a: front view; 5b: 180° view. Gray: residues potentially participating in the epitope category β; black: residues potentially participating in the epitope category α.

51% of the sera did not contain or had less antibodies against scFv105 (β) a scFv of the Vk1-VH1b subtype (different framework). Possible antigenic regions were identified by sequence alignment (FIGS. 3, 4 and 5).

23% of the sera were specific to scFv 903 did, however, neither bind to scFv105 nor to scFv 961 (4). There is only one residue position that differs in both scFvs when compared to scFv903. Thus the respective amino acid in the variable heavy domain of scF 903 (L12) plays a crucial role in the interaction between ADAs and scFv 903. In summary it can be concluded that a) roughly 50% of ADAs bind to an epitope in the interface between variable region and constant region (a), comprising residues at positions 12, 103 and 144 in the variable heavy domain, and b) that mutating these three highly conserved residues significantly lowers binding strength and frequency of pre-existing antibodies to scFvs in general. This generic applicability of the DHP-motif to reduce immunogenicity of scFvs is further supported by the high frequency of Leucine at position 12, Valine at position 103 and Leucine at position 144 in variable heavy chains of human origin. As binding of anti-scFv 903 sera to scFv105 was generally weaker when compared to scFv 903, substitutions of any solvent exposed residue in scFv 903 towards the respective amino acid in scFv105 could potentially eliminate or weaken a B-cell epitope. Of particular interest are residue numbers 101 and 148 in the variable light chain, as these bulky residues participate in the former constant-variable domain interface (table 4).

TABLE 3

Summary table of tested human sera having antibodies against different antigenic regions.

| Category (antigenic region) | % of sera |
|---|---|
| All | 12% |
| α | 35% |
| β | 51% |
| αβ | 23% |
| Nd | 12% |
| None | 4% |
| αγ | 4% |

TABLE 4

Frequency of amino acids in human variable domains at selected positions.

| | Vk1 | | VH | | |
|---|---|---|---|---|---|
| | 101 | 148 | 12 | 103 | 144 |
| A | 0.2 | | 0.1 | | 0.6 |
| C | 0.2 | | | | |
| D | 0.1 | | | | |
| E | 0.1 | 0.5 | | | |
| F | 70.4 | | 1.5 | 0.4 | |
| G | | | | 0.1 | 0.3 |
| H | | | | 0.1 | |
| I | 4.0 | 0.3 | | 4.3 | |
| K | | 92.3 | | 0.1 | 0.6 |
| L | 1.4 | 0.2 | 56.4 | 4.6 | 65.5 |
| M | 0.1 | 0.2 | 0.6 | 12.3 | 10.2 |
| N | | 1.5 | | | |
| P | | 0.1 | | | 0.6 |
| Q | | 0.3 | | | |
| R | | 3.7 | | | 0.9 |
| S | 1.8 | 0.2 | 0.1 | | |
| T | 0.1 | 0.6 | | 4.3 | 19.2 |
| V | 21.5 | | 41.2 | 73.5 | 0.6 |
| W | | | | | 1.5 |
| Y | 0.1 | 0.1 | | | |

While there are shown and described presently preferred embodiments of the invention, it is to be distinctly understood that the invention is not limited thereto but may be otherwise variously embodied and practiced within the scope of the following claims.

The invention claimed is:

1. An antibody variable domain comprising a variable light chain comprising serine (S) at position 99 (Aho numbering), and a variable heavy chain comprising Serine (S) at heavy chain amino acid position 12, Threonine (T) at heavy chain amino acid position 103, and Threonine (T) at heavy chain amino acid position 144 (AHo numbering).

2. The antibody variable domain of claim 1, being an scFv or an Fv fragment.

3. The antibody variable domain of claim 1, being an scFv.

4. The antibody variable domain of claim 1, wherein the Serine (S) at position 99 of the variable light chain is introduced by substitution.

5. A pharmaceutical composition comprising the antibody variable domain of claim 1.

* * * * *